(12) United States Patent
Ou Yang

(10) Patent No.: US 11,351,283 B2
(45) Date of Patent: Jun. 7, 2022

(54) INTELLIGENT STERILIZATION METHOD AND STERILIZATION CONTAINER

(71) Applicant: SHENZHEN UVLED OPTICAL TECHNOLOGY CO., LTD., Shenzhen (CN)

(72) Inventor: Chenyi Ou Yang, Yongzhou (CN)

(73) Assignee: SHENZHEN UVLED OPTICAL TECHNOLOGY CO., LTD., Shenzhen (CN)

( * ) Notice: Subject to any disclaimer, the term of this patent is extended or adjusted under 35 U.S.C. 154(b) by 381 days.

(21) Appl. No.: 16/477,672

(22) PCT Filed: Apr. 29, 2019

(86) PCT No.: PCT/CN2019/085046
§ 371 (c)(1),
(2) Date: Jul. 12, 2019

(87) PCT Pub. No.: WO2020/206766
PCT Pub. Date: Oct. 15, 2020

(65) Prior Publication Data
US 2021/0330845 A1 Oct. 28, 2021

(30) Foreign Application Priority Data
Apr. 11, 2019 (CN) .......................... 201910289526.9

(51) Int. Cl.
*A61L 2/24* (2006.01)
*A61L 2/06* (2006.01)
*A61L 2/10* (2006.01)

(52) U.S. Cl.
CPC ...... *A61L 2/24* (2013.01); *A61L 2/06* (2013.01); *A61L 2/10* (2013.01); *A61L 2202/11* (2013.01);
(Continued)

(58) Field of Classification Search
CPC ..... A61L 2/24; A61L 2/04; A61L 2/06; A61L 2/07; A61L 2/10; A61L 2202/11;
(Continued)

(56) References Cited

U.S. PATENT DOCUMENTS

2017/0260681 A1* 9/2017 Gao .......................... A61L 2/10
2018/0221521 A1* 8/2018 Shur .......................... A61L 2/00

FOREIGN PATENT DOCUMENTS

CN 205048898 U * 2/2016

OTHER PUBLICATIONS

English-language Machine Translation of CN-205048898-U (Year: 2016).*

* cited by examiner

*Primary Examiner* — Timothy C Cleveland
(74) *Attorney, Agent, or Firm* — Li & Cai Intellectual Property (USA) Office

(57) ABSTRACT

An intelligent sterilization method and a sterilization container are disclosed, the intelligent sterilization method comprising: after an intelligent sterilization instruction is issued, the sterilization container sequentially performs the following steps: a sterilizing and drying step, releasing sterilization medium and hot air to an article storage cavity containing a sterilized article, and sterilizing and drying the sterilized article; and a constant temperature aseptic storing step, continuously releasing a small amount of hot air and a small amount of sterilization medium to the article storage cavity to maintain the sterilized article in the article storage cavity at a preset constant temperature and an aseptic condition; wherein the constant temperature is defined as when the sterilized article is in contact with the human body, the human body feels warm and not uncomfortable. The sterilization container includes an article storage cavity, an (Continued)

illumination device, a heating air duct, a microprocessor, and a memory.

15 Claims, 3 Drawing Sheets

(52) U.S. Cl.
CPC ..... *A61L 2202/122* (2013.01); *A61L 2202/14* (2013.01); *A61L 2202/16* (2013.01); *A61L 2202/18* (2013.01); *A61L 2202/26* (2013.01)

(58) Field of Classification Search
CPC ........... A61L 2202/122; A61L 2202/14; A61L 2202/16; A61L 2202/18; A61L 2202/182; A61L 2202/26; D06F 58/32; D06F 58/44; D06F 58/46
See application file for complete search history.

INTELLIGENT STERILIZATION METHOD AND STERILIZATION CONTAINER

BACKGROUND

1. Technical Field

The invention relates to the field of sterilization technology, in particular to an intelligent sterilization method and a sterilization container for articles such as tableware and baby products.

2. Description of Related Art

With the improvement of living standards, people gradually pay attention to the quality of life. Sterilization containers used to sterilize various household items, such as tableware, baby products, etc., have become essential appliances for people. According to the sterilization method, the common ones are ultraviolet and ozone.

These sterilization containers are basically effective in killing bacteria on the sterilized article for sterilization purposes. However, there are still some defects. 1. Inconvenient to use. Some sterilization containers do not have a drying function, and it is impossible to remove the water stains remaining on the sterilized articles. Although some sterilization containers have a drying function, sterilization and drying require separate artificial control. 2, Easy to be contaminated again. Because tableware, baby supplies and other daily necessities are often not used immediately after sterilization, resulting in breed of residual bacteria, or bacteria in the environment and re-contamination of these household items.

SUMMARY

It is an object of the present invention to provide an intelligent sterilization method and a sterilization container to solve the above-mentioned drawbacks of the prior art.

In order to achieve the above object, the technical solution adopted by the present invention is as follows.

An intelligent sterilization method is applied to a sterilization container, wherein the intelligent sterilization method comprises: after an intelligent sterilization instruction is issued, the sterilization container sequentially performs the following steps: a sterilizing and drying step, releasing sterilization medium and hot air in sequence to an article storage cavity containing a sterilized article, and sterilizing and drying the sterilized article; and a constant temperature aseptic storing step: continuously releasing a small amount of hot air and a small amount of sterilization medium to the article storage cavity to maintain the sterilized article in the article storage cavity at a preset constant temperature and an aseptic condition; wherein the constant temperature is defined as when the sterilized article is in contact with the human body, the human body feels warm and not uncomfortable.

Preferably, the sterilization medium is ultraviolet light.

Preferably, the sterilization container is preset with a plurality of different constant temperatures, and in the constant temperature aseptic storing step, the sterilization container acquires an ambient temperature and adaptively selects an appropriate constant temperature according to the ambient temperature.

Preferably, the drying step comprises: releasing hot air to the article storage cavity; when an initial drying time is reached, collecting the intracavity temperature of the article storage cavity; automatically obtaining an extended drying time corresponding to the intracavity temperature of the article storage cavity; and continuously releasing hot air to the article storage cavity until the extended drying time is reached.

Preferably, in the constant temperature aseptic storing step, the method for obtaining the ambient temperature of the sterilization container is to use the intracavity temperature estimation of the article storage cavity.

Preferably, in the step of estimating the ambient temperature using the intracavity temperature estimation of the article storage cavity, the intracavity temperature employed is the temperature at which the initial time is reached in the drying step.

A sterilization container, comprises: an article storage cavity for accommodating a sterilized article; an illumination device for releasing sterilization medium to the article storage cavity; a heating air duct for releasing hot air to the article storage cavity; a microprocessor electrically coupled to the illumination device and the heating air duct, respectively; and a memory storing a computer readable program executable by the microprocessor; wherein the sterilization container performs the steps of the intelligent sterilization method as mentioned above when the computer readable program is executed by the microprocessor.

Preferably, the sterilization container is a portable ultraviolet sterilization container.

Preferably, the heating air duct is an inner circulation type heating air duct.

Compared with the prior art, the present invention has at least the following beneficial effects.

Sterilization, drying and constant temperature aseptic storage can be done automatically with one control, which is highly intelligent and easy to use.

The sterilized article will not be contaminated again due to long time. Since a small amount of the sterilization medium is continuously released after the sterilization and drying are completed, the bacteria can be inhibited from being propagated, so that the sterilized article can be prevented from being contaminated again.

With sterilization identification function, since the sterilized article is always kept at a constant temperature after the sterilization is completed, and the constant temperature can be perceived by user. When the sterilized article is used, the temperature of the sterilized article can be used to make the user know whether the sterilized article is sterilized or not.

Experience is good. Since the sterilized article is always kept at a constant temperature and is better to be kept at this constant temperature, the human body feels warm when it comes to contact with the sterilized article. Therefore, when the sterilized article is used in a cold environment, people do not feel that the sterilized article is cold.

Figure 1:
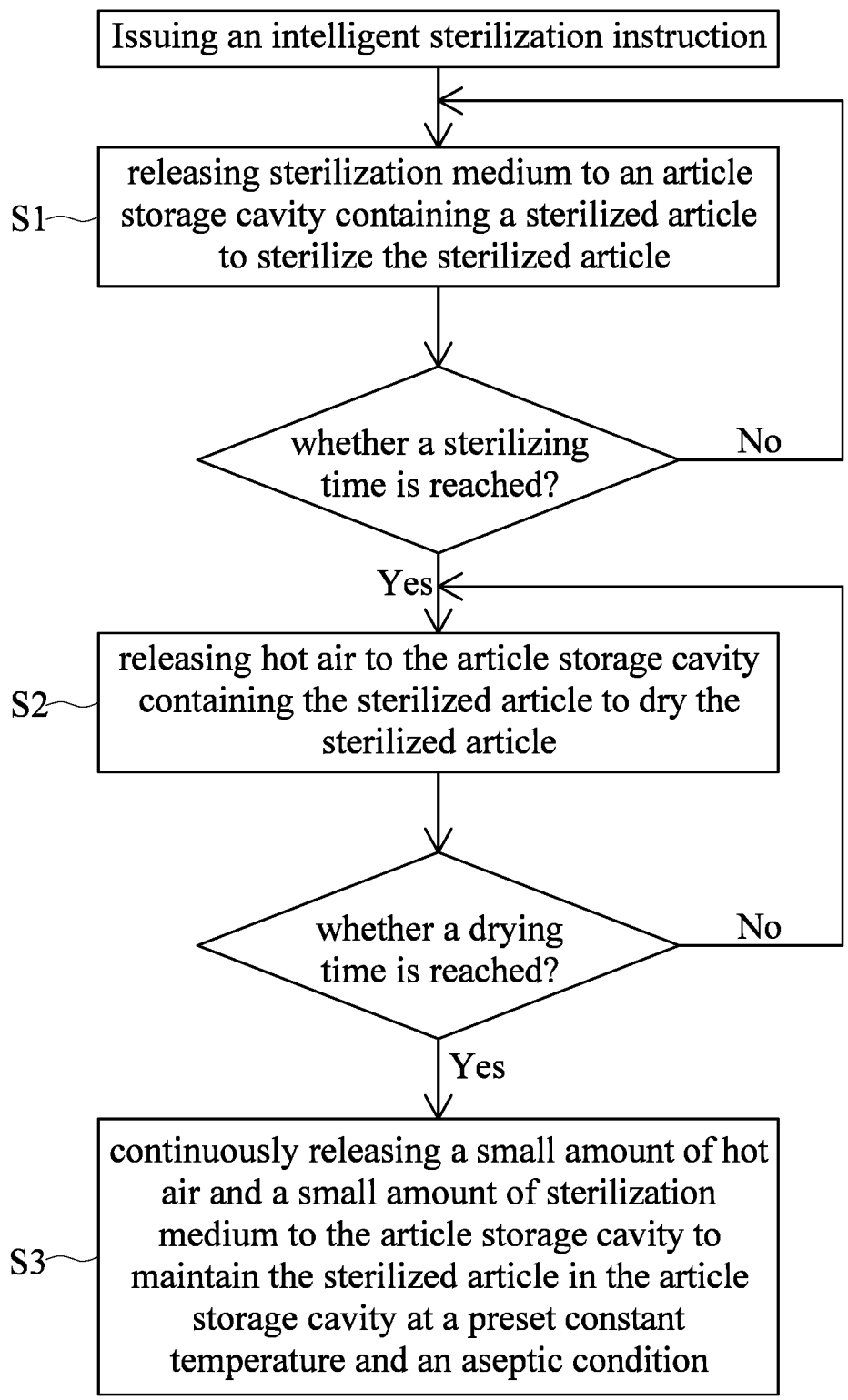
FIG. 1 is a flow chart of the intelligent sterilization method.

Reference numerals: 1, article storage cavity; 2, return air outlet; 3, air outlet; 4, sterilization container body; 5, handle; 6, illumination device (UV LED); 7, air duct; 8, fan.

DESCRIPTION OF THE EXEMPLARY EMBODIMENTS

The invention will be further described below in conjunction with the drawings and embodiments.

This intelligent sterilization method is applied to a sterilization container.

Referring to FIG. 1, the intelligent sterilization method includes the following steps.

The user issues an intelligent sterilization instruction. The intelligent sterilization instruction can be issued through a button set on the sterilization container, or the intelligent sterilization instruction can be issued through a remote control method, such as a remote controller and a mobile phone application.

After the intelligent sterilization instruction is issued, the sterilization container performs the following steps in sequence.

S1, a sterilizing step: releasing sterilization medium to an article storage cavity containing a sterilized article, and sterilizing the sterilized article;

S2, a drying step: releasing hot air to the article storage cavity containing the sterilized article, and drying the sterilized article; and S3, a constant temperature aseptic storing step: continuously releasing a small amount of hot air and a small amount of sterilization medium to the article storage cavity to maintain the sterilized article in the article storage cavity at a preset constant temperature and an aseptic condition; wherein the constant temperature is defined as when the sterilized article is in contact with the human body, the human body feels warm and not uncomfortable.

The sterilization medium herein is preferably, but not limited to, ultraviolet light, ozone, or a combination thereof.

It can be seen that the above sterilization method has at least the following advantages. 1. The sterilization, drying and constant temperature aseptic storage can be automatically completed in one control, which is highly intelligent and convenient to use. 2. Since a small amount of sterilization medium is continuously released after the sterilization and drying is finished, the bacteria can be inhibited from being propagated, so that the sterilized article can be prevented from being contaminated again before use. 3. Since the sterilized article is always kept at a constant temperature after the sterilization is completed, and the constant temperature can be perceived by user. When the sterilized article is used, the temperature of the sterilized article can be used to make the user know whether the sterilized article is sterilized or not. 4. Since the sterilized article is always kept at a constant temperature, and at this constant temperature, the human body feels warm when it comes to contact with the sterilized article. Therefore, in a cold environment, when the sterilized article is used, people do not feel that the sterilized article is cold and thus has a good experience.

Further, the sterilization container is preset with two constant temperatures of 35 degrees Celsius and 38 degrees Celsius. In the constant temperature aseptic storing step, the sterilization container acquires an ambient temperature and adaptively selects an appropriate constant temperature according to the ambient temperature. Specifically, when the ambient temperature is lower than 15 degrees Celsius, a constant temperature of 35 degrees Celsius is selected, and when the ambient temperature is equal to or higher than 15 degrees Celsius, a constant temperature of 38 degrees Celsius is selected. The use of a variety of constant temperature temperatures corresponding to different ambient temperatures, while maintaining the above advantages, can effectively save energy. It should be noted that the constant temperature is not limited to two types, and is not limited to the specific temperature specified above, and may be flexibly set according to actual needs according to the setting principle of the constant temperature in the present invention.

Further, the drying step includes: releasing hot air to the article storage cavity; when an initial drying time is reached, collecting the intracavity temperature of the article storage cavity; automatically obtaining an extended drying time corresponding to the intracavity temperature of the article storage cavity; and continuously releasing hot air to the article storage cavity until the extended drying time is reached. In the exemplary embodiment, the initial drying time is set to 60 minutes, and the extended drying time is divided into four levels according to the intracavity temperature of the article storage cavity when the initial drying time is reached. When the intracavity temperature is lower than 33 degrees Celsius, the drying time is extended by 90 minutes; when the intracavity temperature is between 33-40 degrees Celsius, the drying time is extended by 60 minutes; when the intracavity temperature is between 40-44 degrees Celsius, the drying time is extended by 30 minutes; and when the intracavity temperature is higher than 44 degrees Celsius, the drying time is extended by 0 minutes. It can be seen that the drying method is a two-step intelligent drying method. Compared with the drying method at a fixed time, this two-step intelligent drying method can not only effectively avoid the energy waste caused by "over-drying", but also avoid water stains left on the sterilized article due to "under-drying. It should be noted that the above-mentioned four types, specific temperature values and time values are only a typical embodiment, and these values can be flexibly set as needed. These values require prior experiments to ensure that the sterilized article is just dried when these values are applied.

Further, in the constant temperature aseptic storing step, the sterilization container obtains the ambient temperature by using the intracavity temperature estimation of the article storage cavity. In this way, it is not necessary to additionally install a temperature sensor to detect the ambient temperature, thereby simplifying the circuit and reducing the cost. The calculation method can obtain the ambient temperature by using the "intracavity temperature-ambient temperature correspondence table" obtained by experiments in advance, or can perform correlation calculation, for example, using the cavity temperature minus a constant to obtain the ambient temperature. The specific constants are obtained based on prior experimental statistics.

Further, in the step of estimating the ambient temperature using the intracavity temperature of the article housing cavity, the intracavity temperature employed is the temperature at which the initial time is reached in the drying step. In this way, sharing the same intracavity temperature with the determination of the extended drying time can simplify the process and optimize the calculation efficiency.

Figure 2:
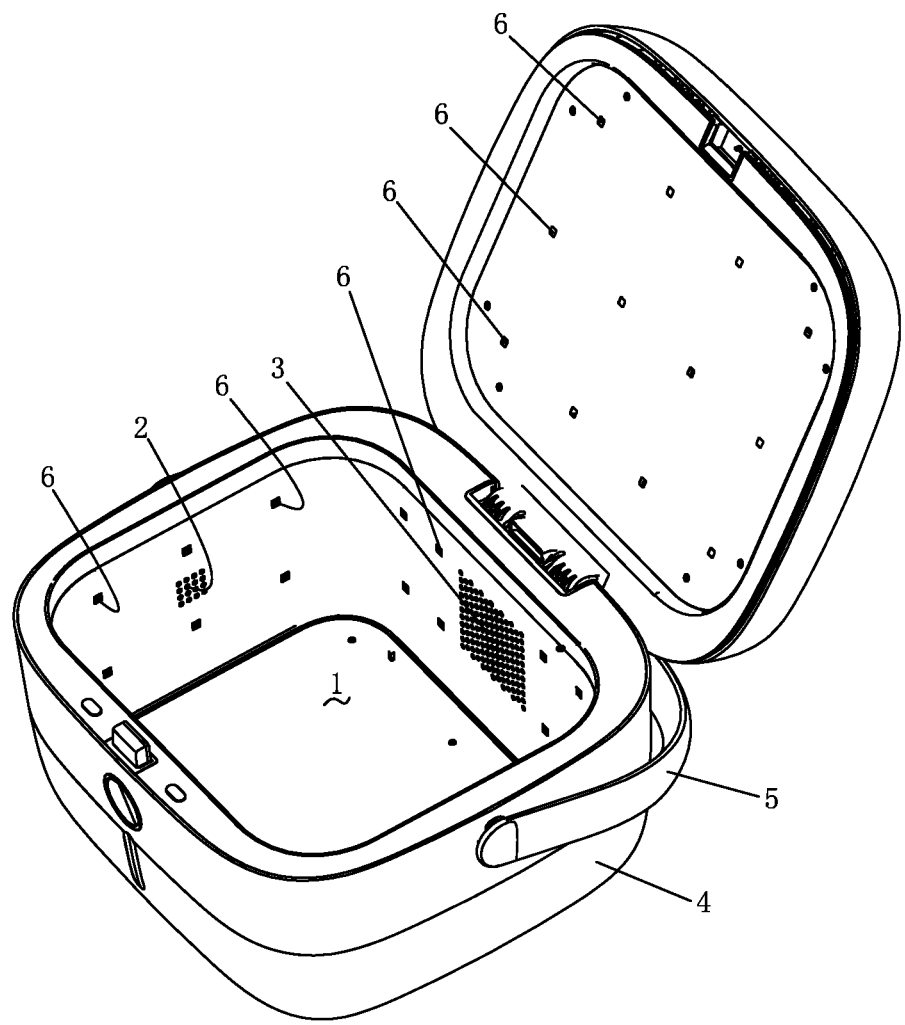
FIG. 2 is a schematic structural view of the article storage cavity, the illumination device, and the heating air duct of the sterilization container.
Figure 3:
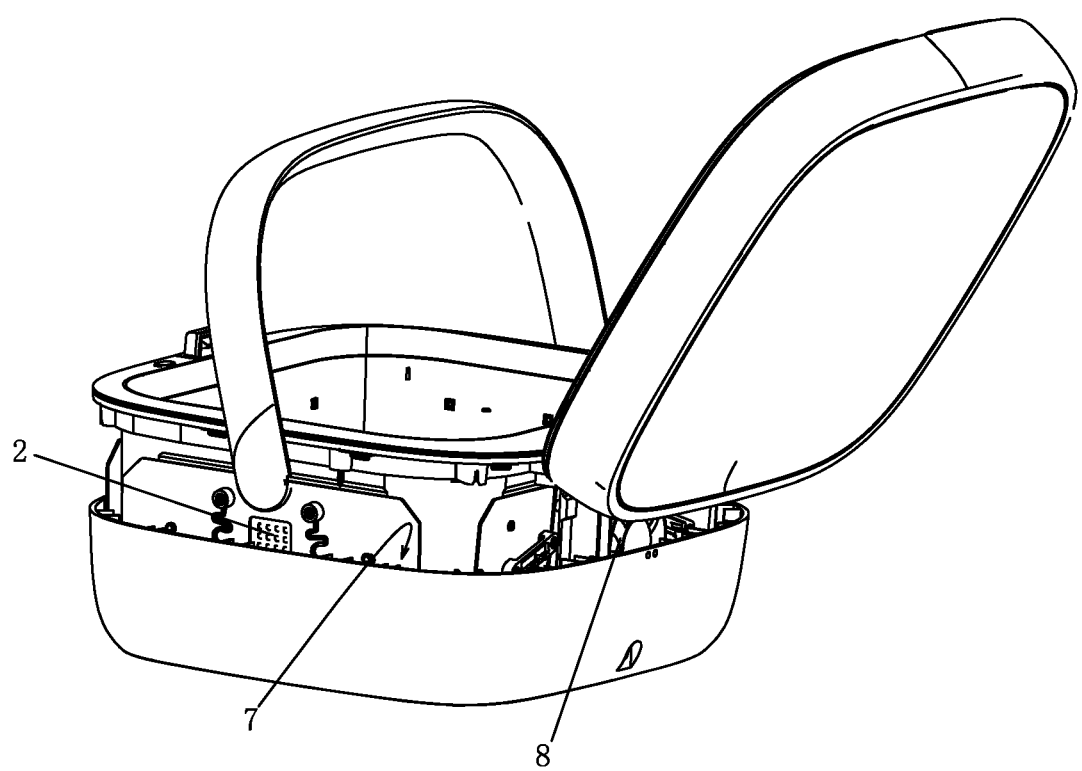
FIG. 3 is a schematic view of the fan and the air duct in the heating air duct.

Referring to FIG. 2 and FIG. 3, the sterilization container includes: an article storage cavity 1 for accommodating an article to be sterilized, an illumination device 6 disposed on a cavity wall of the article storage cavity 1 for releasing ultraviolet light (sterilization medium) to the article storage cavity 1, and a heating air duct disposed on a cavity wall of the article storage cavity 1 for releasing hot air to the article storage cavity 1. The heating air duct includes: a return air outlet 2, an air outlet 3, an air duct 7, a fan 8, and the electric heating element (not shown). When the fan 8 is in operation, the air of the article storage cavity 1 is sucked into the air duct 7 from the return air outlet 2, heated by the electric heating element, and then delivered to the article storage cavity 1 from the air outlet 3. The article storage cavity 1 dries the sterilized article in the article storage cavity 1, and the heating air duct circulates the air in the article storage cavity 1 without introducing ambient air, that is, an inner circulation type heating air duct, which can save energy for heating consumption.

The sterilization container further includes a microprocessor (not shown) electrically connected to the illumination device 6 and the heating air duct, respectively, and a memory storing a computer readable program executable by the microprocessor (not shown). When the computer readable program is executed by the microprocessor, the sterilization container performs the steps of the above-described intelligent sterilization method. The memory may be an on-chip memory of the microprocessor or an external stand-alone memory.

The sterilization container is a portable UV sterilization container that can be used not only at home but also for use in the office or when going out. The sterilization container body 4 is provided with a handle 5.

The present invention has been described in detail with reference to the preferred embodiments thereof, and the detailed description is not to be construed as limiting the scope of the invention. Various refinements, equivalent transformations, and the like performed by the above-described embodiments under the present invention should be included in the scope of the present invention.

What is claimed is:

1. An intelligent sterilization method for a sterilization container, comprising after an intelligent sterilization instruction is issued, the sterilization container sequentially performing the following steps:
   a sterilizing and drying step, releasing sterilization medium and hot air in sequence to an article storage cavity containing an article to be sterilized to sterilize and dry the article; and
   a constant temperature aseptic storing step, continuously releasing hot air and sterilization medium to the article storage cavity to maintain the sterilized article in the article storage cavity at a preset constant temperature and an aseptic condition;
   wherein the sterilization container acquires an ambient temperature and adaptively selects an appropriate constant temperature according to the ambient temperature to assign as the preset constant temperature.

2. The intelligent sterilization method according to claim 1, wherein the sterilization medium is ultraviolet light.

3. The intelligent sterilization method according to claim 1, wherein the sterilization container is preset with a plurality of different constant temperatures.

4. The intelligent sterilization method according to claim 3, wherein the sterilizing and drying step comprises:
   releasing hot air to the article storage cavity;
   when an initial drying time is reached, collecting an intracavity temperature of the article storage cavity;
   automatically obtaining an extended drying time corresponding to the intracavity temperature of the article storage cavity; and
   continuously releasing hot air to the article storage cavity until the extended drying time is reached.

5. The intelligent sterilization method according to claim 3, wherein in the constant temperature aseptic storing step, a method for obtaining the ambient temperature of the sterilization container is to use an intracavity temperature estimation of the article storage cavity by using an intracavity temperature-ambient temperature correspondence table or performing a correlation calculation.

6. The intelligent sterilization method according to claim 4, wherein in the constant temperature aseptic storing step, a method for obtaining the ambient temperature of the sterilization container is to use an intracavity temperature estimation of the article storage cavity by using an intracavity temperature-ambient temperature correspondence table or performing a correlation calculation.

7. The intelligent sterilization method according to claim 6, wherein in the step of estimating the ambient temperature using the intracavity temperature estimation of the article storage cavity, the intracavity temperature employed is the temperature at which the initial drying time is reached in the sterilizing and drying step.

8. A sterilization container, comprising:
   an article storage cavity configured to accommodate a sterilized article;
   an illumination device configured to release sterilization medium to the article storage cavity;
   a heating air duct configured to release hot air to the article storage cavity;
   a microprocessor electrically coupled to the illumination device and the heating air duct, respectively; and
   a memory storing a computer readable program executable by the microprocessor;
   wherein the sterilization container performs the steps of the intelligent sterilization method according to claim 1 when the computer readable program is executed by the microprocessor.

9. The sterilization container according to claim 8, wherein the sterilization container is preset with a plurality of different constant temperature.

10. The sterilization container according to claim 9 wherein the sterilizing and drying step comprises:
    releasing hot air to the article storage cavity;
    when an initial drying time is reached, collecting an intracavity temperature of the article storage cavity;
    automatically obtaining an extended drying time corresponding to the intracavity temperature of the article storage cavity; and
    continuously releasing hot air to the article storage cavity until the extended drying time is reached.

11. The sterilization container according to claim 9, wherein in the constant temperature aseptic storing step, a method for obtaining the ambient temperature of the sterilization container is to use an intracavity temperature estimation of the article storage cavity by using an intracavity temperature-ambient temperature correspondence table or a performing a correlation calculation.

12. The sterilization container according to claim 11, wherein in the step of estimating the ambient temperature using the intracavity temperature estimation of the article storage cavity, the intracavity temperature employed is the temperature at which an initial drying time is reached in the sterilizing and drying step.

13. The sterilization container according to claim 8 wherein the sterilization container is a portable ultraviolet sterilization container.

14. The sterilization container according to claim 13, wherein the heating air duct is an inner circulation type heating air duct.

15. The sterilization container according to claim 8 wherein the sterilization medium is ultraviolet light.

* * * * *